(12) United States Patent
Crudden et al.

(10) Patent No.: US 9,132,576 B2
(45) Date of Patent: Sep. 15, 2015

(54) METHOD OF MANUFACTURING ANTIMICROBIAL IMPLANTS OF POLYETHERETHERKETONE

(71) Applicant: DiFusion Technologies, Inc., Georgetown, TX (US)

(72) Inventors: Joseph J. Crudden, Hudson, NH (US); Derrick Johns, Austin, TX (US)

(73) Assignee: DiFusion Technologies, Inc., Georgetown, TX (US)

( * ) Notice: Subject to any disclaimer, the term of this patent is extended or adjusted under 35 U.S.C. 154(b) by 0 days.

(21) Appl. No.: 14/471,329

(22) Filed: Aug. 28, 2014

(65) Prior Publication Data

US 2014/0366362 A1    Dec. 18, 2014

Related U.S. Application Data

(63) Continuation of application No. 13/512,702, filed as application No. PCT/US2010/059868 on Dec. 10, 2010, now Pat. No. 8,821,912.

(60) Provisional application No. 61/285,719, filed on Dec. 11, 2009, provisional application No. 61/300,629, filed on Feb. 2, 2010.

(51) Int. Cl.
*A61F 2/44*    (2006.01)
*B29C 45/00*    (2006.01)
(Continued)

(52) U.S. Cl.
CPC .............. *B29C 45/0013* (2013.01); *A61L 27/18* (2013.01); *A61L 27/54* (2013.01); *B29B 13/022* (2013.01); *B29B 13/06* (2013.01); *B29C 43/003* (2013.01); *B29C 43/26* (2013.01); *B29C 43/32* (2013.01); *B29C 43/52* (2013.01); *B29C 45/0001* (2013.01); *B29C 45/0005* (2013.01); *B29C 45/0053* (2013.01); *A61L 2300/104* (2013.01); *A61L 2300/404* (2013.01); *B29K 2071/00* (2013.01); *B29K 2105/0011* (2013.01); *B29K 2105/04* (2013.01); *B29K 2105/12* (2013.01);
(Continued)

(58) Field of Classification Search
None
See application file for complete search history.

(56) References Cited

U.S. PATENT DOCUMENTS

| 4,088,737 A | 5/1978 | Thomas et al. |
| 4,596,574 A | 6/1986 | Urist |

(Continued)

FOREIGN PATENT DOCUMENTS

| BY | 11260 C1 | 10/2008 |
| CA | 2171703 A1 | 4/1995 |

(Continued)

OTHER PUBLICATIONS

Russian Communication, with English translation, issued Jan. 12, 2015 in co-pending Russian patent application 2012126078/15(040280).

(Continued)

*Primary Examiner* — Isaac Shomer
(74) *Attorney, Agent, or Firm* — Nields, Lemack & Frame, LLC

(57) ABSTRACT

Methods of fabricating implantable medical devices, preferably with PEEK, having antimicrobial properties, are disclosed. The antimicrobial effect is produced by incorporating ceramic particles containing antimicrobial metal cations into molten PEEK resin, which is subsequently allowed to cool and set in its final shape achieved by injection molding, cutting and machining or other techniques.

12 Claims, 1 Drawing Sheet

(51) Int. Cl.

| | | |
|---|---|---|
| *A61L 27/18* | (2006.01) | |
| *A61L 27/54* | (2006.01) | |
| B29B 13/02 | (2006.01) | |
| B29B 13/06 | (2006.01) | |
| B29C 43/00 | (2006.01) | |
| B29C 43/26 | (2006.01) | |
| B29C 43/32 | (2006.01) | |
| B29C 43/52 | (2006.01) | |
| B29K 71/00 | (2006.01) | |
| B29K 105/00 | (2006.01) | |
| B29K 709/02 | (2006.01) | |
| B29L 31/00 | (2006.01) | |
| B29K 105/04 | (2006.01) | |
| B29K 105/12 | (2006.01) | |
| B29K 105/16 | (2006.01) | |
| B29K 307/04 | (2006.01) | |
| B29K 505/14 | (2006.01) | |

(52) U.S. Cl.
CPC ......... *B29K 2105/16* (2013.01); *B29K 2307/04* (2013.01); *B29K 2505/14* (2013.01); *B29K 2709/02* (2013.01); *B29K 2995/0056* (2013.01); *B29K 2995/0072* (2013.01); *B29L 2031/7532* (2013.01); *Y10T 29/4998* (2015.01)

(56) References Cited

U.S. PATENT DOCUMENTS

| | | | |
|---|---|---|---|
| 4,612,337 A | 9/1986 | Fox, Jr. et al. | |
| 4,615,705 A | 10/1986 | Scales et al. | |
| 4,775,585 A | 10/1988 | Hagiwara et al. | |
| 4,775,586 A | 10/1988 | Bohrn et al. | |
| 4,861,808 A | 8/1989 | Billington et al. | |
| 4,906,464 A | 3/1990 | Yamamoto et al. | |
| 4,911,898 A | 3/1990 | Hagiwara et al. | |
| 4,911,899 A | 3/1990 | Hagiwara et al. | |
| 4,923,450 A | 5/1990 | Maeda et al. | |
| 4,938,955 A | 7/1990 | Niira et al. | |
| 4,938,958 A | 7/1990 | Niira et al. | |
| 4,957,817 A | 9/1990 | Chau et al. | |
| 4,959,268 A | 9/1990 | Hagiwara et al. | |
| 5,003,638 A | 4/1991 | Miyake et al. | |
| 5,100,671 A | 3/1992 | Maeda et al. | |
| 5,151,122 A | 9/1992 | Atsumi et al. | |
| 5,180,585 A | 1/1993 | Jacobson et al. | |
| 5,192,590 A | 3/1993 | Sherman | |
| 5,256,390 A | 10/1993 | Hu | |
| 5,266,534 A | 11/1993 | Atsumi et al. | |
| 5,294,634 A | 3/1994 | Yamaguchi | |
| 5,296,238 A | 3/1994 | Sugiura et al. | |
| 5,474,797 A | 12/1995 | Sioshansi et al. | |
| 5,478,563 A | 12/1995 | Erami | |
| 5,492,763 A | 2/1996 | Barry et al. | |
| 5,522,904 A | 6/1996 | Moran et al. | |
| 5,556,699 A | 9/1996 | Niira et al. | |
| 5,595,750 A | 1/1997 | Jacobson et al. | |
| 5,607,464 A | 3/1997 | Trescony et al. | |
| 5,609,629 A | 3/1997 | Fearnot et al. | |
| 5,614,568 A | 3/1997 | Mawatari et al. | |
| 5,647,858 A | 7/1997 | Davidson | |
| 5,688,561 A | 11/1997 | Ichikawa et al. | |
| 5,709,870 A | 1/1998 | Yoshimura et al. | |
| 5,731,087 A | 3/1998 | Fan et al. | |
| 5,753,251 A | 5/1998 | Burrell et al. | |
| 5,756,145 A | 5/1998 | Darouiche | |
| 5,770,255 A | 6/1998 | Burrell et al. | |
| 5,783,570 A | 7/1998 | Yokota et al. | |
| 6,015,816 A | 1/2000 | Kostyniak et al. | |
| 6,090,732 A | 7/2000 | Ito et al. | |
| 6,180,606 B1 | 1/2001 | Chen et al. | |
| 6,248,342 B1 | 6/2001 | Trogolo et al. | |
| 6,267,590 B1 | 7/2001 | Barry et al. | |
| 6,296,863 B1 | 10/2001 | Trogolo et al. | |
| 6,436,422 B1 | 8/2002 | Trogolo et al. | |
| 6,471,993 B1 | 10/2002 | Shastri et al. | |
| 6,582,715 B1 * | 6/2003 | Barry et al. | 424/422 |
| 6,585,767 B1 | 7/2003 | Holley et al. | |
| 6,720,006 B2 | 4/2004 | Hanke et al. | |
| 6,723,428 B1 | 4/2004 | Foss et al. | |
| 6,866,859 B2 | 3/2005 | Trogolo et al. | |
| 6,946,196 B2 | 9/2005 | Foss | |
| 6,984,392 B2 | 1/2006 | Bechert et al. | |
| 6,994,883 B2 | 2/2006 | Layrolle et al. | |
| 7,270,813 B2 | 9/2007 | Shimp et al. | |
| 7,354,605 B2 | 4/2008 | Trogolo et al. | |
| 7,357,949 B2 | 4/2008 | Trogolo et al. | |
| 8,652,645 B2 | 2/2014 | Dingeldein et al. | |
| 8,821,912 B2 * | 9/2014 | Crudden et al. | 424/423 |
| 8,840,914 B2 * | 9/2014 | Crudden et al. | 424/423 |
| 2002/0099449 A1 | 7/2002 | Speitling | |
| 2003/0031687 A1 | 2/2003 | Falder et al. | |
| 2004/0109937 A1 | 6/2004 | Jennissen et al. | |
| 2005/0058682 A1 | 3/2005 | Sharratt | |
| 2005/0064176 A1 | 3/2005 | Terry | |
| 2005/0149196 A1 | 7/2005 | Zucherman et al. | |
| 2005/0170070 A1 | 8/2005 | Layrolle et al. | |
| 2005/0203529 A1 | 9/2005 | Boehm, Jr. et al. | |
| 2006/0052479 A1 | 3/2006 | Cougoulic | |
| 2006/0069438 A1 | 3/2006 | Zucherman et al. | |
| 2006/0161256 A1 | 7/2006 | Ziegler et al. | |
| 2006/0177379 A1 | 8/2006 | Asgari | |
| 2006/0259020 A1 * | 11/2006 | Sharratt | 606/1 |
| 2006/0265065 A1 * | 11/2006 | Bagga et al. | 623/17.11 |
| 2006/0280803 A1 | 12/2006 | Kumar et al. | |
| 2007/0015110 A1 | 1/2007 | Zhang et al. | |
| 2007/0031515 A1 | 2/2007 | Stucky et al. | |
| 2007/0110825 A1 | 5/2007 | Taniguchi et al. | |
| 2007/0267029 A1 | 11/2007 | Mason | |
| 2007/0276337 A1 | 11/2007 | Trieu | |
| 2007/0299472 A1 | 12/2007 | Brighton | |
| 2008/0032119 A1 | 2/2008 | Feldhahn et al. | |
| 2008/0033572 A1 | 2/2008 | D'Antonio et al. | |
| 2008/0063671 A1 | 3/2008 | Morris et al. | |
| 2008/0208340 A1 | 8/2008 | Boyd et al. | |
| 2008/0249637 A1 | 10/2008 | Asgari | |
| 2008/0258337 A1 | 10/2008 | Ajbani et al. | |
| 2009/0012612 A1 | 1/2009 | White et al. | |
| 2009/0238850 A1 | 9/2009 | Greener | |
| 2010/0010632 A1 * | 1/2010 | Bourges et al. | 623/16.11 |
| 2010/0099058 A1 | 4/2010 | Wang | |
| 2010/0114317 A1 | 5/2010 | Lambrecht et al. | |
| 2010/0215643 A1 | 8/2010 | Clevenger et al. | |
| 2011/0022181 A1 | 1/2011 | Kasahara et al. | |
| 2012/0141599 A1 | 6/2012 | Johns et al. | |
| 2012/0315340 A1 | 12/2012 | Crudden et al. | |
| 2012/0323339 A1 | 12/2012 | Olalde Graells et al. | |
| 2013/0004585 A1 | 1/2013 | Crudden et al. | |
| 2013/0037991 A1 | 2/2013 | Crudden et al. | |
| 2013/0073042 A1 | 3/2013 | Ghiselli et al. | |

FOREIGN PATENT DOCUMENTS

| | | |
|---|---|---|
| CN | 1732025 A | 2/2006 |
| CN | 100360193 C | 1/2008 |
| CN | 101234304 A | 8/2008 |
| CN | 101238166 A | 8/2008 |
| DE | 3228849 A1 | 2/1984 |
| DE | 10055465 A1 | 5/2002 |
| EA | 011594 B1 | 4/2009 |
| EP | 0116865 A1 | 8/1984 |
| EP | 0253663 A2 | 1/1988 |
| EP | 0722660 A2 | 7/1996 |
| EP | 1813292 A1 | 8/2007 |
| FR | 2848856 A1 | 6/2004 |
| JP | 2004-523302 A | 8/2004 |
| RU | 2313370 C2 | 12/2007 |
| RU | 2338557 C2 | 11/2008 |
| WO | 84/01721 A1 | 5/1984 |
| WO | 99/07326 A2 | 2/1999 |
| WO | 00/30697 A1 | 6/2000 |
| WO | 00/32247 A2 | 6/2000 |
| WO | 00/64505 A1 | 11/2000 |

(56) References Cited

FOREIGN PATENT DOCUMENTS

| WO | 03/086495 | A1 | 10/2003 |
| WO | 2004/058319 | A1 | 7/2004 |
| WO | 2006/069677 | A2 | 7/2006 |
| WO | 2007/019461 | A2 | 2/2007 |
| WO | 2008/039488 | A2 | 4/2008 |
| WO | WO 2008037751 | A2 * | 4/2008 |
| WO | 2008/150867 | A2 | 12/2008 |
| WO | 2009/099559 | A2 | 8/2009 |
| WO | 2010/114827 | A1 | 10/2010 |
| WO | 2014/152649 | A1 | 9/2014 |

OTHER PUBLICATIONS

Office Action mailed Jan. 10, 2013 in co-pending U.S. Appl. No. 13/511,176.
Final Rejection mailed Oct. 23, 2013 in co-pending U.S. Appl. No. 13/511,176.
Office Action mailed May 20, 2014 in co-pending U.S. Appl. No. 13/511,176.
Office Action mailed Oct. 9, 2014 in co-pending U.S. Appl. No. 13/696,346.
International Search Report/Written Opinion mailed May 13, 2010 in co-pending PCT application No. PCT/US 10/29180.
International Preliminary Report on Patentability dated Dec. 6, 2011 in co-pending PCT application No. PCT/US 10/29180.
Chinese Communication issued Sep. 26, 2012 in co-pending Chinese patent application No. CN 201080015851.3.
European communication mailed Feb. 6, 2014 in co-pending European patent application No. 10759287.5.
Russian Communication, with English translation, issued Oct. 9, 2013 in co-pending Russian patent application No. RU 2011144020.
Russian communication dated Apr. 14, 2014 in co-pending Russian patent application No. 2011144020/15(066044).
International Search Report and Written Opinion mailed Aug. 19, 2011 in co-pending PCT application No. PCT/US2010/058009.
International Preliminary Report on Patentability mailed Jun. 7, 2012 in co-pending PCT application No. PCT/US2010/058009.
Extended European Search Report mailed May 21, 2013 in co-pending European patent application No. EP 10833925.0.
Chinese Communication issued Dec. 3, 2013 in co-pending Chinese patent application No. CN 201080062338.X.
Chinese communication, with English translation, issued Jul. 1, 2014 in co-pending Chinese patent application No. 201080062338.X.
Russian communication, with English translation, dated Sep. 15, 2014 in co-pending Russian patent application No. 2012126078/15(040280).
International Search Report and Written Opinion mailed Aug. 25, 2011 in corresponding PCT application No. PCT/US2010/059868.
International Preliminary Report on Patentability mailed Jun. 21, 2012 in corresponding PCT application No. PCT/US2010/059868.
European Communication mailed Aug. 27, 2013 in corresponding European patent application No. EP 10836743.4.
English translation of Chinese Communication issued Oct. 30, 2013 in corresponding Chinese patent application No. CN 201080063584.7.
Chinese communication, with English translation, issued Jun. 17, 2014 in corresponding Chinese patent application No. CN 201080063584.7.
Russian Communication, with English translation, issued Nov. 20, 2013 in corresponding Russian patent application No. RU 2012129171.
Russian communication dated Apr. 17, 2014 in corresponding Russian patent application No. 2012129171/15(045686).
International Search Report and Written Opinion mailed Jan. 9, 2012 in co-pending PCT application No. PCT/US2011/035468.
International Preliminary Report on Patentability mailed Aug. 7, 2012 in co-pending PCT application No. PCT/US2011/035468.
European Communication mailed Sep. 4, 2013 in co-pending European patent application No. EP 11778401.7.
Chinese Communication issued Jan. 6, 2014 in co-pending Chinese patent application No. CN 201180023035.1.
Chinese communication, with English translation, issued Jul. 7, 2014 in co-pending Chinese patent application No. CN 201180023035.1.
Canadian communication dated Apr. 9, 2014 in co-pending Canadian patent application No. 2,795,836.
Antimicrobial Agents and Chemotherapy, Dec. 2005, vol. 49, No. 12, p. 4853-4859, "Role of Silver Ions in Destabilization of Intermolecular Adhesion Forces Measured by Atomic Force Microscopy in Staphylococcus epidermidis Biofilms", Chaw, et al.
DiFusion Technologies research paper, created Oct. 14, 2013, "Novel Orthopedic Implant Material Protects Osteoblast Viability in the Presence of Biofilm-Forming MRSA", 4 pages.
Emerging Infectious Diseases, vol. 7, No. 2, Mar.-Apr. 2001, pp. 277-281, "Biofilms and Device-Associated Infections", Donlan.
Clinical Microbiology Reviews, Apr. 2002, vol. 15, No. 2, pp. 155-166, Focus, "Bacterial Adhesion: Seen Any Good Biofilms Lately?", Dunne, Jr., et al.
"Antimicrobial Efficacy of a novel Orthobiologic PEEK in treating Surgical Site Spine Infections", http://www.difusiontech.com/wp-content/uploads/NASS-Summer-Conference_2013-Abstract_final2.pdf, NASS Summer Session, Aug. 2-5, 2013, Naples, FL, 2 pages, Eastlack, et al.
"Exploring the efficacy of a self-sterilizing orthobiologic PEEK as a viable biomaterial for spinal surgery", http://www.nassannualmeeting.org/Documents/AMB_FinalProgram.pdf, Abstract, NASS Annual Meeting, Oct. 9-12, 2013 NewOrleans, LA, 3 pages, Eastlack, et al.
The Journal of Biological Chemistry, vol. 263, No. 13, May 5, 1988, pp. 6276-6280, "Regulation of the Enterotoxin B Gene in *Staphylococcus aureus*", Gaskill, et al.
Neurosurg. Focus, vol. 10, No. 4, 2001, 7 pages, "Bone Graft Substitutes for the Promotion of Spinal Arthrodesis", Helm, et al.
Journal of the Physical Society of Japan, vol. 77, No. 6, Jun. 2008, 064712, "Photoluminescence of the Dehydrated Ag-type Zeolite A Packed under Air", pp. 064712-1-064712-7, Hoshino, et al.
Ann Nutr Metab., 1993, 37(5):245-252, 2 page abstract, "Impaired mechanical strength of bone in experimental copper deficiency", Jonas, et al.
European Cells and Materials, vol. 8, 2004, pp. 37-57, "Concise Review of Mechanisms of Bacterial Adhesion to Biomaterials and of Techniques Used in Estimating Bacteria-Material Interactions", Katsikogianni, et al.
J Bone Miner Res., Nov. 1992, vol. 7(11), pp. 1281-1289, 1 page Abstract, http://www.ncbi.nlm.nih.gov/pubmed/1334616, "Zeolite A increases proliferation, differentiation, and transforming growth factor beta production in normal adult human osteoblast-like cells in vitro", Keeting, et al.
Medical Design Technology Online, Jan. 28, 2010, 5 pages, http://www.mdtmag.com/scripts/ShowPR.asp?PUBCODE=046&ACCT=0006305&ISSUE . . . , "Taking a PEEK at Material Options for Orthopedics", Kinbrum.
National Institute of Standards and Technology (NIST) recommended practice guide, Special Publication 960-17, Sep. 2006, "Porosity and Specific Surface Area Measurements for Solid Materials", 91 pages, Klobes, et al.
Clin. Orthop. Relat. Res., Nov.-Dec. 1981, vol. 161, pp. 154-162, 1 page Abstract, "Antibacterial and osteoinductive properties of demineralized bone matrix treated with silver", Kramer, et al.
Medicaldevice-network.com, Jul. 2011, http://www.medicaldevice-network.com/features/feature128303, "PEEK performance: a next-generation biomaterial", 5 pages, Kurtz.
Biomaterials, vol. 28, 2007, pp. 4845-4869, "PEEK biomaterials in trauma, orthopedic, and spinal implants", Kurtz, et al.
The Journal of Nutrition, 2002, http://jn.nutrition.org/content/132/10/3135.full.pdf+html, Nutrient Requirements, "Bone Morphology, Strength and Density Are Compromised in Iron-Deficient Rats and Exacerbated by Calcium Restriction", pp. 3135-3141, Medeiros, et al.
Journal of Polymer Science: Part B: Polymer Physics, 2004, vol. 42, pp. 1548-1563, "Poly(ether ether ketone)/Poly (aryl ether sulfone) Blends: Melt Rheological Behavior", Nandan, et al.

(56) References Cited

OTHER PUBLICATIONS

BMC Musculoskeletal Disorders, 2013, 14:187, http://www.biomedcentral.com/1471-2474/14/187, 11 pages, "*Staphylococcus aureus* biofilms decrease osteoblast viability, inhibits osteogenic differentiation, and increases bone resorption in vitro", Sanchez, Jr., et al.

J. Phys. Chem. A, 2000, vol. 104, pp. 7473-7483, "Colors of Ag+-Exchanged Zeolite A.", Seifert, et al.

Rothman-Simeone—The Spine, 2011, 6th Edition, vol. II, Chapter 98, Garlin S., ed., "Postoperative Spinal Infections", 53 pages, Smith, et al.

United States Environmental Protection Agency, Silver-Copper Zeolite Data Review, Feb. 15, 1994, 3 pages.

Office Action—Restriction—mailed Jan. 23, 2014 in co-pending U.S. Appl. No. 13/260,571.

Office Action mailed May 12, 2014 in co-pending U.S. Appl. No. 13/260,571.

Chinese communication, with English translation, issued Sep. 30, 2014 in co-pending Chinese patent application No. 201080062338.X.

Final Rejection mailed Oct. 16, 2014 in co-pending U.S. Appl. No. 13/260,571.

Final Rejection mailed Jan. 5, 2015 in co-pending U.S. Appl. No. 13/511,176.

Zinc Toxicity in Humans, 2007, Elsevier B.V. publication, pp. 1-7, Jerome NRIAGU, School of Public Health, University of Michigan.

Mexican communication, with English translation, dated Apr. 17, 2015 in co-pending Mexican patent application No. MX/a/2012/012710.

Chinese communication, with English translation, mailed Mar. 30, 2015 in co-pending Chinese patent application No. 201180023035.1.

International Search Report and Written Opinion mailed Jul. 21, 2014 in co-pending PCT application No. PCT/US14/27576.

International Preliminary Report on Patentability mailed Apr. 8, 2015 in co-pending PCT application No. PCT/US14/27576.

Journal of the Brazilian Chemical Society, vol. 19,. No. 1, Sao Paolo, 2008, pp. 1-11, downloaded from the interenet Mar. 1, 2013, "Preparation and characterization of poly(ether ether ketone) derivatives", Conceicao, et al.

Net Motion, Inc., copyright 2003, http://www.netmotion.com/htm_files/wh_properties.htm#chem, pp. 1-8, downloaded from internet Mar. 1, 2013, All you want to know about Polyetheretherketone (PEEK), Chemical Resistance of PEEK, PEEK and Polymer chemical resistance.

VICI AG International, 2013, VICI Jour-Technical Support, Chemical Resistance of PEEK and Other Polymers, Chart displaying PEEK and Polymer Chemical Resistance, 3 pages.

The Structure and Synthesis of Zeolite Molecular Sieves, Jilin University Press, Aug. 1987, 1st Edition, pp. 6 and 8, 4 pages, Xu, et al.

Office Action mailed Apr. 22, 2015 in co-pending U.S. Appl. No. 13/260,571.

Notice of Allowance mailed Apr. 9, 2015 in co-pending U.S. Appl. No. 13/696,346.

European communication dated May 27, 2015 in corresponding European patent application No. 108367434.

29th Edition of the Kunststoff Taschenbuch, 2004, pp. 514-517, Oberbach, et al.

\* cited by examiner

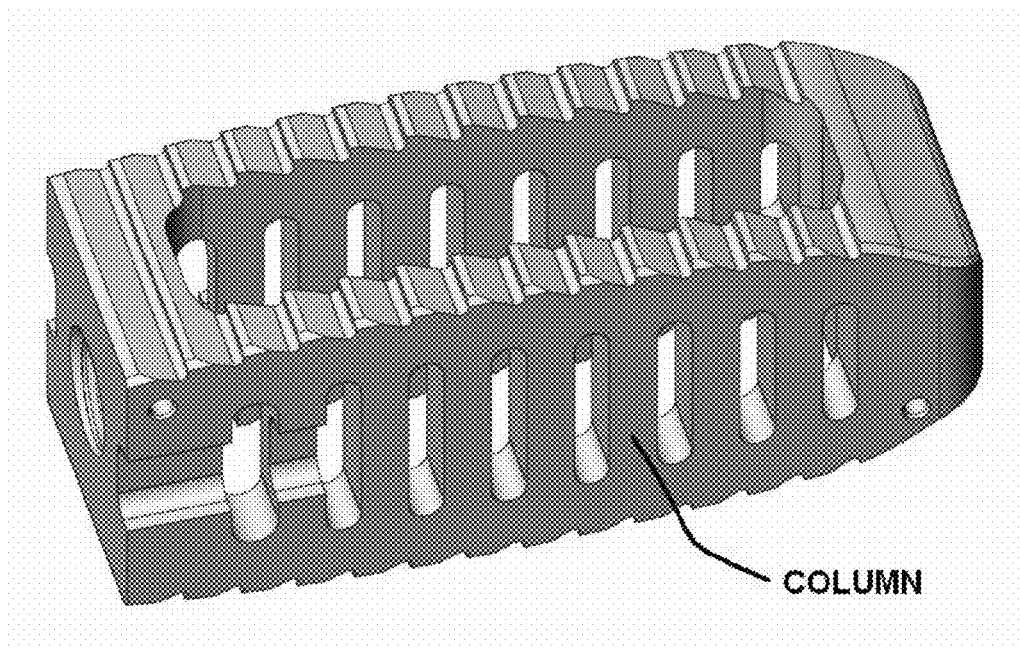

METHOD OF MANUFACTURING ANTIMICROBIAL IMPLANTS OF POLYETHERETHERKETONE

This application is a continuation of U.S. patent application Ser. No. 13/512,702 filed Aug. 30, 2012, which is a 371 of International Application No. PCT/US2010/059868 filed Dec. 10, 2010, which claims priority of U.S. Provisional Application Ser. No. 61/285,719 filed Dec. 11, 2009 and 61/300,629 filed Feb. 2, 2010, the disclosures of which are incorporated herein by reference.

BACKGROUND

Implantable medical devices are implanted into the body for various reasons, including orthopedics (e.g., hip replacement, spinal procedures, knee replacement, bone fracture repair, etc.). In view of the structural integrity requirements of such devices, materials of fabrication are limited, and conventionally include metal, plastic and composites.

The benefits derived from these devices are often offset by infection, which can lead to sepsis and death. The most common organisms causing infections are *Staphylococcus epidermidis* and *Staphylococcus aureus*. Other gram-positive bacteria, gram-negative bacteria and fungal organisms also are problematic. Of particular concern is Methicillin-resistant *Staphylococcus aureus* (MRSA), a type of *staphylococcus* bacteria that are resistant to many antibiotics. As a result, MRSA infections are more difficult to treat than ordinary staph infections, and have become a serious problem.

Many pathogenic bacteria can form multicellular coatings, called biofilms on bioengineered implants. Biofilms can facilitate the proliferation and transmission of microorganisms by providing a stable protective environment. These biofilms, when well developed, can disseminate bacterial planktonic showers which can result in broad systemic infection.

Bioengineered materials act as excellent hosts for the formation of bacterial biofilms. Occasionally, the implant itself carries the infecting organism, and the implants develop very tenacious biofilms seeded by infecting organisms. When this occurs, usually the implant must be removed, the patient must be treated with a prolonged course of one or more antibiotics in an effort to cure the infection, and a new implant is then re-implanted. This obviously subjects the patient to additional trauma and pain, and is extremely expensive.

Accordingly, much research has been devoted toward preventing colonization of bacterial and fungal organisms on the surfaces of orthopedic implants by the use of antimicrobial agents, such as antibiotics, bound to the surface of the materials employed in such devices. For example, silver is a powerful, natural antibiotic and preventative against infections. Acting as a catalyst, it disables the enzyme that one-cell bacteria, viruses and fungi need for their oxygen metabolism. They suffocate without corresponding harm occurring to human enzymes or parts of the human body chemistry. The result is the destruction of disease-causing organisms in the body. Silver disrupts bacteria membranes, inter-membrane enzymes, and DNA transcription.

Ceramics such as zeolite function as a cation cage, being able to be loaded with silver and other cations having antimicrobial properties. Metal zeolites can be used as an antimicrobial agent, such as by being mixed with the resins used as thermoplastic materials to make the implantable devices, or as coatings to be applied to the devices; see, for example, U.S. Pat. No. 6,582,715, the disclosure of which is hereby incorporated by reference. The antimicrobial metal zeolites can be prepared by replacing all or part of the ion-exchangeable ions in zeolite with ammonium ions and antimicrobial metal ions. Preferably, not all of the ion-exchangeable ions are replaced.

One particular thermoplastic resin that has been found to be useful in an implant is polyetheretherketone (PEEK). This thermoplastic polymer has an aromatic backbone, interconnected by ketone and ether functionality. PEEK is suitable for implants because its modulus closely matches that of bone, and is resistant to chemical and radiation damage. Grades of PEEK approved for implantation are very pure and inert and need to pass stringent cytotoxicity testing before being allowed to be implanted into mammals.

The ISO 10993 set entails a series of standards for evaluating the biocompatibility of a medical device prior to a clinical study. These documents were preceded by the Tripartite agreement and are a part of the harmonization of the safe use evaluation of medical devices. Those standards include:

ISO 10993-1:2003 Biological evaluation of medical devices Part 1: Evaluation and testing ISO 10993-2:2006 Biological evaluation of medical devices Part 2: Animal welfare requirements ISO 10993-3:2003 Biological evaluation of medical devices Part 3: Tests for genotoxicity, carcinogenicity and reproductive toxicity ISO 10993-4:2002/Amd 1:2006 Biological evaluation of medical devices Part 4: Selection of tests for interactions with blood ISO 10993-5:2009 Biological evaluation of medical devices Part 5: Tests for in vitro cytotoxicity ISO 10993-6:2007 Biological evaluation of medical devices Part 6: Tests for local effects after implantation ISO 10993-7:1995 Biological evaluation of medical devices Part 7: Ethylene oxide sterilization residuals ISO 10993-8:2001 Biological evaluation of medical devices Part 8: Selection of reference materials ISO 10993-9:1999 Biological evaluation of medical devices Part 9: Framework for identification and quantification of potential degradation products ISO 10993-10:2002/Amd 1:2006 Biological evaluation of medical devices Part 10: Tests for irritation and delayed-type hypersensitivity ISO 10993-11:2006 Biological evaluation of medical devices Part 11: Tests for systemic toxicity ISO 10993-12:2007 Biological evaluation of medical devices Part 12: Sample preparation and reference materials (available in English only)

ISO 10993-13:1998 Biological evaluation of medical devices Part 13: Identification and quantification of degradation products from polymeric medical devices ISO 10993-14:2001 Biological evaluation of medical devices Part 14: Identification and quantification of degradation products from ceramics ISO 10993-15:2000 Biological evaluation of medical devices Part 15: Identification and quantification of degradation products from metals and alloys ISO 10993-16:1997 Biological evaluation of medical devices Part 16: Toxicokinetic study design for degradation products and leachables ISO 10993-17:2002 Biological evaluation of medical devices Part 17: Establishment of allowable limits for leachable substances ISO 10993-18:2005 Biological evaluation of medical devices Part 18: Chemical characterization of materials ISO/TS 10993-19:2006 Biological evaluation of medical devices Part 19: Physio-chemical, morphological and topographical characterization of materials ISO/TS 10993-20:2006 Biological evaluation of medical devices Part 20: Principles and methods for immunotoxicology testing of medical devices At high processing temperatures, metal zeolite can release moisture if it is not extremely dry. This moisture can cause the formation of voids in the polymer melt and can contribute to the decomposition of the PEEK polymer and to oxidation of metals, such as silver, copper and/or zinc, incorporated into the zeolite antimicrobial. Although the presence of voids may not be critical for certain non-load bearing applications, the absence of voids is critical for load-bearing applications such as spinal repair.

If the process of incorporating metal zeolites is carried out in air, severe oxidation can occur as the temperature is raised, and moisture and oxygen come into contact with the metal ions. Silver will rapidly darken to a dark brown or black color. Also, the incorporation of significant quantities of metal zeolites into the PEEK polymer can affect the viscosity and rheology of the composition.

The present disclosure is based on the finding that it is possible, under conditions of high temperature and high shear, to incorporate antimicrobial zeolite, such as silver zeolite, into PEEK, such as by mixing doped metal zeolites into molten PEEK (melting point between 300 and 400° C., depending on purity), followed by molding and processing of the composite blend. The result is the provision of medical devices such as implants with effective antimicrobial activity in order to reduce the growth of bacteria and risk of infection.

SUMMARY

The shortcomings of the prior art have been overcome by the present disclosure, which relates to methods of fabricating implantable medical devices, preferably with PEEK, having antimicrobial properties. The antimicrobial effect is produced by incorporating ceramic particles containing antimicrobial metal cations into molten PEEK resin, which is subsequently allowed to cool and set in its final shape achieved by injection molding, cutting and machining or other techniques.

The rate of release of metallic ions is governed by the extent of loading of the plastic with ceramic particles containing metal ions and the loading of metal in the ceramic material. The electrolyte concentration in blood and body fluids is relatively constant and will cause ion exchange with ions such as silver, copper and zinc, and others from the surface of the implant, which deactivate or kill gram positive and gram negative organisms, including *E. coli* and *Staphylococcus aureus*. Effective antimicrobial control of a six-log reduction of microorganisms is achieved, for example, at metal zeolite concentrations of 4% or greater. The devices are implantable into animals, particularly humans. Spinal implants are particularly contemplated.

BRIEF DESCRIPTION OF THE DRAWING

FIG. 1 is a perspective view of a cervical spacer in accordance with certain embodiments.

DETAILED DESCRIPTION

Embodiments disclosed herein relate to the processing of ceramics, preferably zeolites, as a cation cage in combination with medical implants to deliver and dose one or more antimicrobial cations. In addition to zeolite, other suitable ceramic antimicrobial materials include hydroxy apatite, zirconium phosphates and other ion-exchange ceramics.

Suitable cations include silver, copper, zinc, mercury, tin, lead, gold, bismuth, cadmium, chromium and thallium ions, and combinations thereof, with silver, zinc and/or copper being preferred. Either natural zeolites or synthetic zeolites can be used to make the zeolites used in the embodiments disclosed herein.

"Zeolite" is an aluminosilicate having a three dimensional skeletal structure that is represented by the formula: $XM_{2/n}O \cdot Al_2O_3 \cdot YsiO_2 \cdot ZH_2O$ wherein M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, and others.

In addition, silicate materials such as metal doped phosphate glass, bioactive glass such as 45S5 and BG can be processed to deliver a suitable dose of antimicrobial cations.

The following process and handling conditions are required for processing antimicrobial PEEK implants with the desired properties.

Material Handling

PEEK is a high melting point material that has a melting point of approximately 340° C. and must be processed at 360° C. to 400° C. to enable incorporation of metal zeolite powders and extruding or molding of the composite blend. At these high temperatures, release of any entrapped moisture can cause the formation of voids in the polymer melt. This can contribute to decomposition of the PEEK polymer and to oxidation of metals incorporated into the zeolite antimicrobial, reducing antimicrobial efficacy. Additionally, presence of voids can significantly degrade the properties of the final product. For material produced for load-bearing spinal implants, the minimization of the size and number of any voids is critical in maintaining the mechanical properties of the final product. Therefore, it is essential to remove residual moisture from the raw materials utilized in producing the implant, PEEK and antimicrobial powder (composite blend components). The silver zeolite powder should be heated to about 400° C. at atmospheric pressure, and held there for sufficient time for the bound water to be released. If the powder is spread thinly, moisture release will be more efficient, and a holding time of 30 to 60 minutes is suitable. The silver zeolite can also be dried at lower temperatures under reduced pressure. It is preferable that the composite blend components be dried in a clean environment to less than 0.1% moisture by weight prior to processing. Moreover, it is imperative to maintain the material in an anhydrous environment prior to and during processing.

The antimicrobial powder is extremely hygroscopic, requiring the material to be sealed in its original packaging prior to any usage. Exposure to ambient air has to be minimal during pre-blending operations. As an added precaution, the feeder powder hopper needs to be purged with dry nitrogen immediately before and after loading.

The PEEK material should be dried between 120° C.-130° C. for 12 hours (or at a time/temperature equivalent) before running any compounding operation. This ensures that the residual moisture of the PEEK pellets is less than 0.1% moisture by weight prior to processing.

Post-Processed Packaging: The materials need to be packaged in moisture barrier bags immediately after compounding.

Compounding Equipment

To achieve a high degree of consistency, a twin-screw extruder can be utilized for blending PEEK with required additives. The additive is gravimetrically metered into molten PEEK just prior to entering the extruder screws to obtain the desire additive loading. The use of twin-screw extrusion improves filler distribution and wet-out, and results in a more reproducible rheological behavior.

A specific example of preferred equipment used for compounding is described below:
Extruder Line: 30 mm
Screw design: 30-3
Die set-up: 2 hole
Acceptable Range of Pellet Length (inches): 0.100-0.135
Acceptable Range of Pellet Diameter (inches): 0.085-0.120
One suitable extruder is a Leistritz ZSE twin screw extruder.
Compression Molding Near-net shaped compounded PEEK blanks suitable for secondary machining operations can be produced using the compression molding process. Compression molding is a method of molding preheated compounded PEEK polymer pellets or pre-forms into predefined shapes in pressurized, heated mold cavities. Compression molding is a high-volume, high-pressure method suitable for molding complex shapes. This process wastes relatively little material when compared to machining devices from extruded rods.
Machining PEEK implants can be manufactured to final shape by removing material with machining process such as turning, boring, drilling, milling, broaching, sawing, shaping, planing and/or reaming. These machining processes can be manual or automated through the use of computer controlled machining centers.

The thermal conductivity of all polymeric materials is lower than that of metals, so heat build-up during machining is rapid. A cleaner cut and more open surface can be achieved if the bit is cooled and run at a slower rate. Machined PEEK surfaces can smear and "skin" if the PEEK surface temperature significantly rises while the material is being machined into implants, possibly affecting the release of cations. To optimize the compounded PEEK surface finish, a clean cut and "open" surface structure is desired. One method to achieve the desired surface finish is to cool the cutting tool with cold, clean compressed air in conjunction with optimized tool cutting speed and feed rates. Moreover, cooling rates can have a profound effect on the crystallinity of PEEK, which may be critical to optimize the rate of release of metallic ions. By adjusting the cooling rate during fabrication, the percent crystallinity of the implant material was carefully controlled.

Machining and finishing operations on PEEK materials are prone to propagating residual stresses. Before machining, it is recommended that components formed from PEEK be annealed to relieve stress. During machining or finishing, further stresses may be built-up within the material by localized heating at the cutting point. Therefore, if a large amount of machining and finishing is to be carried out on a component, a second annealing procedure could be required. Based on the desired outcome of the annealing process (removal of stresses or thermal history or the optimization of crystalline structure) annealing processes recommended by the PEEK material manufacturer should be requested and followed.

Additional precautions can be taken to prevent surface contamination of machined compounded PEEK devices by dedicating machine tools as "PEEK only" and locating the machine tools in areas of the manufacturing facility specifically dedicated to the machining of medical grade PEEK.
Injection Molding Finished or significantly finished compounded PEEK devices can be manufactured using the injection molding process. The injection molding process produces parts from compounded PEEK polymers by feeding compounded PEEK pellets into a heated barrel (400° C.) where the molten compounded PEEK is mixed and forced into a heated mold cavity that is maintained at temperatures between about 175° C. and 205° C. Once injected into to the mold, the molten compounded PEEK cools to a temperature below 343° C. and hardens to the shape of the mold cavity. By monitoring and closely controlling the desired temperature (between about 175° C. to 205° C.) set-point of the molds, significant increases in part feature and tolerance control and minimization of surface skinning can be achieved.
Optimal Zeolite Loading The amount of metal zeolite incorporated into the resin should also be an amount effective for promoting antimicrobial activity; e.g., a sufficient amount so as to prevent or inhibit the growth and eradicate bacterial and fungal organisms. At the same time incorporation of significant quantities of metal zeolites into the peek polymer melt can affect the viscosity and rheology of the composition. Therefore, a processing window was established that allowed for sufficient zeolite to be loaded without adversely affecting the bulk properties of the final product.

Suitable amounts of zeolite in the resin range from about 0.01 to 20.0 wt. %. Optimal loading was found to range from 0.1 to about 10.0 wt. %. The tightly controlled and monitored dimensions of the pellets produced from the optimal loading conditions are shown below in Table I. The finished pellet color is an important indicator if severe oxidation occurred or moisture came into contact with the metal ions during the high temperature process. Pure PEEK is light tan in color while properly processed zeolite containing PEEK is brown in color. In cases where oxidation has occurred, the silver will rapidly darken to a dark brown or black color.

TABLE I

Average pellet length and diameter

| Zeolite Loading | Average Pellet Diameter(inch) | Average Pellet Length (inch) | Color |
| --- | --- | --- | --- |
| 0.5% | 0.090 | 0.126 | Brown |
| 1.0% | 0.093 | 0.127 | Brown |
| 2.0% | 0.093 | 0.127 | Brown |
| 4.0% | 0.091 | 0.125 | Brown |

Confirmation of Embedded Zeolites

Scanning electron micrographs (SEM) of the samples revealed that dispersion of the zeolite particles in the composites were satisfactorily uniform. The SEM images show that the samples are highly loaded, consistent with the target loading rates.

Pyrolysis was utilized for quantitative determination of the loading of silver metal zeolite. A small accurately weighed sample of the PEEK/silver zeolite composite was placed in a ceramic crucible and burned with a propane torch. While plain PEEK burns away completely leaving no residue using this method, PEEK loaded with metal zeolites will burn off and leave behind a powdery residue. The amount of silver zeolite loading can then be determined gravimetrically. The amount of silver present can be confirmed by extracting the silver from the residue and determining the amount of silver in the extraction solution by graphite furnace AA or ICP.
Quantification of Eluted Silver The elutable ionic silver content from samples with different loading rates was determined by chemical analysis using graphite furnace atomic absorption spectroscopy. 1"×1"

sample coupons were immersed into 40 ml of 0.8% sodium nitrate solution for a duration of 24 hours. The amount of silver eluted from different loadings is listed in Table II.

TABLE II

Amount of silver eluted from different loading

| Zeolite Loading | Eluted Silver Concentration (ug/L) | | |
| --- | --- | --- | --- |
| | Run 1 | Run 2 | Run 3 |
| 0.5% | 1 | <1 | <1 |
| 1.0% | <1 | <1 | <1 |
| 2.0% | 1.5 | 2.1 | 1.3 |
| 4.0% | 4.8 | 10 | 4.7 | conditions

Elution of other antimicrobial metals can be determined similarly.

Antimicrobial Efficacy

It is not self-evident that silver or other metal zeolite incorporated into molten PEEK will show adequate antimicrobial control when the surface of the material is exposed to a microbial challenge. Bacterial challenge tests were performed with a gram negative (*E. Coli*) and a gram positive (*Staphylococcus aureus*) microorganism with two different loadings (2% and 4%) being tested. The results show that for both organisms, a 4% loading was effective in controlling the colony forming units (CFU) of bacteria after an exposure of 24 hours. As Table III highlights, control samples without any zeolite showed no bacterial reduction, while the 4% loadings showed at least a six log reduction of microorganism over the stated period of time.

TABLE III

Antimicrobial Efficacy of against a gram negative and a gram positive organism

| Zeolite Loading | Test Organism | Average Reduction in CFU |
| --- | --- | --- |
| 0%(Control Sample) | *E. Coli* | No Reduction |
| 2% | *E. Coli* | 77.0% |
| 4% | *E. Coli* | 99.99992% |
| 0%(Control Sample) | *S. Aureus* | No Reduction |
| 2% | *S. Aureus* | 30.5% |
| 4% | *S. Aureus* | 99.99998% |

Radiopacity

One disadvantage of PEEK implants is that because of PEEK's radiolucent properties implanted devices made from PEEK do not show up well in X-ray images. Thus, identification of the precise location and integrity of the implant and observation of other important characteristics from X-rays can be difficult. One method that has been used to overcome this drawback is the addition of barium sulfate to the compounding mix. Although devices can be radiopaque due to the addition of barium sulfate to PEEK, the addition of the required amounts of barium sulfate for the desired radiopacity tends to weaken the strength of the resulting device. Thus, the use of an implant made from a composition of barium sulfate and PEEK provides an undesirable tradeoff between the desired mechanical properties of the device and its radiopacity. The materials disclosed herein display radiopaque properties even at low loading levels of silver zeolite when viewed under x-ray. This is an important additional benefit that can be derived without sacrificing antimicrobial effectiveness or mechanical integrity of the material.

Enhanced cell attachment

Zeolite at the surface of the implant can significantly increase osteoblast cell attachment due to the presence of negatively charged silicates present in the zeolites. A significant drawback of PEEK products oftentimes is the lack of cell adhesion at the implant site due to the inherent inertness of PEEK. This problem can be suitably alleviated through the availability of by negatively charged silicates at the implant surface. The zeolite structure is inherently negatively charged. These silicates attract proteins containing the RGD peptide sequence with the correct confirmation, leading to the attachment and proliferation of bone forming osteoblast cells. This starts a cascading process that eventually results in significant bone growth.

Surface Roughness Optimization

PEEK is very impermeable to moisture so only material in the surface layer no deeper than the diameter of a zeolite particle will be accessible for silver elution. If the silver in this region were deactivated or otherwise converted into insoluble complexes the materials might well be ineffective as antimicrobial materials. So process conditions need to be carefully monitored and followed to maintain silver effectiveness on the implant surface. Effectiveness can be monitored quantitatively by measuring the elutable silver using an ICP and ensuring that the level is well above the reported minimum biofilm growth inhibitory concentration of 0.1 ppm of silver. 20 ppb silver has been shown to be active in the lab and formulations show antimicrobial activity below 5 ppb. Moreover, while the bulk solution concentration may be 5 ppb, the activity of cations close to the surface must necessarily be better.

Surface color can also be used as a qualitative measure for monitoring process conditions. Deactivated or otherwise converted silver will change color from brown to black or a mixture of black-brown.

Additionally, surface roughness can be optimized to improve osteogenic properties of the implant. In-vitro studies have shown that all parameters (adhesion, proliferation, alkaline phosphatase activity, synthesis of bone matrix proteins and mineralization) effecting bone growth appear to be influenced by the surface finish of the material. Common manufacturing techniques such as abrasive blasting (bead blasting, sandblasting, sodablasting, cryogenic $CO_2$ blasting etc.), scraping or sanding with inert materials can be utilized to control the surface roughness to optimize both silver elution and cell growth. Atomic force microscopy (AFM) or Profilometry can be utilized to calculate the average surface roughness in nanometers and this value can be correlated to bone growth parameters from vitro cell testing results to get the optimum range of surface roughness.

Increase in Vascularization

Early lumbar and cervical spacers had a monolithic construction in the majority of the cases. The goal was to create polymeric mimics of allograft cortical bones, which had been the previous gold standard for fusion. The current evolution of implant design has been toward openings between inner and outer surfaces for vascularization of the new bone mass. The cavity of the spacer is important as it receives outside material (fillers) and may be a carrier of pathogens. The columns of the implants disclosed herein has been designed so that it allows for a mechanically robust implant, while increasing vascularization pathways, and making large areas available for silver elution.

A specific example of the design is shown in FIG. 1. As can be seen from the figure, the columnar design allows for a significant increase in surface area compared to a monolithic construction. This leads to a significantly enhanced silver elution profile as well as increasing the pathways for vascularization.

Adding Porosity

If desired, in certain embodiments the PEEK can be made porous with suitable porosities including porosities between 50% and 85% by volume. Porosity can be imparted using a pore forming agent such as sodium chloride, to create a porous polymer comprising a plurality of interconnected pores, by processes known in the art. Average pore size is generally greater than 180 microns in diameter, suitably between about 300 and about 700 microns.

Resin Reinforcement

If desired, in certain embodiments the PEEK can be reinforced with a reinforcing material such as ceramic or carbon fiber. This can be produced by dispersing the reinforcing material in the PEEK polymer matrix, such as by twin screw compounding of implantable PEEK polymer with carbon fibers. The resulting carbon fiber-reinforced product can be used to direct injection mold final devices and near net shapes, or it can be extruded into stock shapes for machining. The incorporation of fibers or other suitable reinforcing material(s) provides high wear resistance, a Young's modulus of 12 GPa (matching the modulus of cortical bone) and providing sufficient strength to permit its use in very thin implant designs which distribute the stress more efficiently to the bone. The amount of reinforcing material such as carbon fiber incorporated into the PEEK can be varied, such as to modify the Young's modulus and flexural strength. One suitable amount is 30 wt. % carbon fiber.

What is claimed is:

1. A method of making a load-bearing antimicrobial implant, comprising drying polyetheretherketone resin to a residual moisture content of less than 0.1% moisture by weight, heating said dried polyetheretherketone resin to a temperature effective to melt said resin, blending into said molten resin a metal zeolite that has been dried to a residual moisture content of less than 0.1% moisture by weight, cooling said blend, forming said blend into said implant, and roughening the surface of said implant.

2. The method of claim 1, wherein said temperature effective to melt said resin is from about 360 to about 400° C.

3. The method of claim 1, wherein said metal zeolite comprises silver zeolite.

4. The method of claim 1, wherein said resin is dried by heating it to a temperature between about 120° and 130° C.

5. The method of claim 1, wherein said zeolite is dried at a temperature of about 400° C.

6. The method of claim 1, wherein the amount of zeolite blended into said resin is from about 0.01 to about 20.0 wt %.

7. The method of claim 1, wherein said polyetheretherketone is porous.

8. The method of claim 7, wherein said polyetheretherketone has a porosity between 50% and 85% by volume.

9. The method of claim 1, wherein said polyetheretherketone is reinforced.

10. The method of claim 1, wherein said polyetheretherketone is reinforced with carbon fiber.

11. The method of claim 1, wherein the metal in said metal zeolite is selected from the group consisting of silver, copper, zinc, mercury, tin, lead, gold, bismuth, cadmium, chromium and thallium.

12. The method of claim 1, wherein said surface roughness is created by abrasive blasting.

* * * * *